(12) United States Patent
Yamada

(10) Patent No.: US 12,317,629 B2
(45) Date of Patent: May 27, 2025

(54) IMAGE PICKUP UNIT, ENDOSCOPE, AND METHOD OF MANUFACTURING IMAGE PICKUP UNIT

(71) Applicant: OLYMPUS MEDICAL SYSTEMS CORP., Tokyo (JP)

(72) Inventor: Junya Yamada, Kawasaki (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 97 days.

(21) Appl. No.: 18/379,238

(22) Filed: Oct. 12, 2023

(65) Prior Publication Data

US 2024/0038817 A1   Feb. 1, 2024

Related U.S. Application Data

(63) Continuation of application No. PCT/JP2021/024598, filed on Jun. 29, 2021.

(51) Int. Cl.
| | | |
|---|---|---|
| *H01L 23/544* | (2006.01) | |
| *H04N 23/50* | (2023.01) | |
| *H10F 39/00* | (2025.01) | |
| *A61B 1/00* | (2006.01) | |
| *A61B 1/05* | (2006.01) | |

(52) U.S. Cl.
CPC .......... *H10F 39/811* (2025.01); *H01L 23/544* (2013.01); *H04N 23/555* (2023.01); *A61B 1/0011* (2013.01); *A61B 1/051* (2013.01); *H01L 2223/54426* (2013.01)

(58) Field of Classification Search
CPC ... H10F 39/811; H04N 23/555; H01L 23/544; H01L 2223/54426; A61B 1/0011; A61B 1/051
See application file for complete search history.

(56) References Cited

U.S. PATENT DOCUMENTS

| | | | |
|---|---|---|---|
| 2017/0127921 A1* | 5/2017 | Motohara | H04N 23/57 |
| 2020/0337539 A1 | 10/2020 | Shimohata et al. | |
| 2022/0382091 A1* | 12/2022 | Nakano | G02F 1/133512 |

FOREIGN PATENT DOCUMENTS

| | | |
|---|---|---|
| JP | H04085737 U1 | 7/1992 |
| JP | 2012018993 A | 1/2012 |

(Continued)

OTHER PUBLICATIONS

International Search Report dated Sep. 21, 2021 issued in PCT/JP2021/024598.

*Primary Examiner* — Jae N Noh

(74) *Attorney, Agent, or Firm* — Scully, Scott, Murphy & Presser, P.C.

(57) ABSTRACT

An image pickup unit includes a stacked device in a substantially rectangular parallelepiped shape including an external electrode, and a three-dimensional wiring board including a bonding electrode and an alignment mark on a bottom surface of a recess on a first principal surface and a projection, on a side surface, projecting in a first direction parallel to a wall surface of the recess, in which the external electrode of the stacked device that is disposed in the recess is bonded to the bonding electrode, and on the bottom surface, an area of a region in which a first region where the bonding electrode is virtually moved in the first direction and the alignment mark are superposed on each other is less than 50% of an area of the alignment mark.

8 Claims, 6 Drawing Sheets

(56) References Cited

FOREIGN PATENT DOCUMENTS

| | | |
|---|---|---|
| JP | 2012042671 A | 3/2012 |
| JP | 6533787 B2 | 6/2019 |
| JP | 2021087032 A | 6/2021 |
| WO | 2015082328 A1 | 6/2015 |
| WO | 2019138462 A1 | 7/2019 |

* cited by examiner

IMAGE PICKUP UNIT, ENDOSCOPE, AND METHOD OF MANUFACTURING IMAGE PICKUP UNIT

CROSS REFERENCE TO RELATED APPLICATION

This application is a continuation application of PCT/JP2021/024598 filed on Jun. 29, 2021, the entire contents of which are incorporated herein by this reference.

BACKGROUND OF THE INVENTION

1. Field of the Invention

The present invention relates to an image pickup unit with an image pickup member disposed in a recess of a three-dimensional wiring board, an endoscope including the image pickup unit with the image pickup member disposed in the recess of the three-dimensional wiring board, and a method of manufacturing the image pickup unit with the image pickup member disposed in the recess of the three-dimensional wiring board.

2. Description of the Related Art

It is important to reduce a diameter of an image pickup unit disposed in a distal end portion of an insertion portion of an endoscope for alleviating invasiveness.

Japanese Patent Application Laid-Open Publication No. 2012-18993 discloses a stacked device manufactured using a wafer-level packaging method for efficiently manufacturing an image pickup unit with a small diameter. In the wafer-level packaging method, the stacked device is produced by dicing a stacked wafer in which a plurality of lens wafers each including a plurality of lenses and a plurality of image pickup devices are adhesively bonded.

International Publication No. 2015/082328 (Japanese Patent No. 6533787) discloses an image pickup unit in which a stacked device including an image pickup device is housed in a recess of a three-dimensional wiring board. By using an MID (molded interconnect device) as the three-dimensional wiring board, the manufacturing process can be simplified.

SUMMARY OF THE INVENTION

An image pickup unit of an embodiment includes: a stacked device in a substantially rectangular parallelepiped shape including: a light receiving surface and a back surface on a side opposite to the light receiving surface; and an external electrode, on the back surface, that outputs an image pickup signal; and a three-dimensional wiring board including: a first principal surface and a side surface orthogonal to the first principal surface; a bonding electrode and an alignment mark on a bottom surface of a recess on the first principal surface; and a projection, on the side surface, projecting in a first direction parallel to a wall surface of the recess, in which the external electrode of the stacked device that is disposed in the recess is bonded to the bonding electrode, and on the bottom surface, an area of a region in which a first region where the bonding electrode is virtually moved in the first direction and the alignment mark are superposed on each other is less than 50% of an area of the alignment mark.

An endoscope of another embodiment includes an image pickup unit. The image pickup unit includes: a stacked device in a substantially rectangular parallelepiped shape including: a light receiving surface and a back surface on a side opposite to the light receiving surface; and an external electrode, on the back surface, that outputs an image pickup signal; and a three-dimensional wiring board including: a first principal surface and a side surface orthogonal to the first principal surface; a bonding electrode and an alignment mark on a bottom surface of a recess on the first principal surface; and a projection, on the side surface, projecting in a first direction parallel to a wall surface of the recess, in which the external electrode of the stacked device that is disposed in the recess is bonded to the bonding electrode, and on the bottom surface, an area of a region in which a first region where the bonding electrode is virtually moved in the first direction and the alignment mark are superposed on each other is less than 50% of an area of the alignment mark.

A method of manufacturing an image pickup unit of another embodiment includes producing a plurality of three-dimensional wiring boards each including a first principal surface and a side surface orthogonal to the first principal surface, and a plurality of bonding electrodes and an alignment mark on a bottom surface of a recess on the first principal surface, using an injection molding method in which resin is injected into a mold via runners respectively extending from the side surfaces and then through irradiation with a laser and film-forming by plating; cutting the plurality of three-dimensional wiring boards at each of the runners into individual pieces of the three-dimensional wiring boards each including, on the side surface, a gate cut projecting in a first direction parallel to a wall surface of the recess; causing the gate cut of each of the three-dimensional wiring boards to abut on one surface of a jig; on the bottom surface, using the alignment mark with an area of a region superposed on a first region where the bonding electrode is virtually moved in the first direction is less than 50% of an area of the alignment mark, performing positioning between the bonding electrode and an external electrode of a stacked device in a substantially rectangular parallelepiped shape that includes a light receiving surface and a back surface, and on the back surface, the external electrode that outputs an image pickup signal, and bonding the external electrode and the bonding electrode.

DETAILED DESCRIPTION OF THE PREFERRED EMBODIMENTS

Hereinafter, embodiments of the present invention will be described with reference to the drawings.

Note that the drawings based on the embodiments are schematic illustrations. The relation between the thickness and the width of each portion, the ratio in thickness of each portion, and the like differ from the actual relation, ratio, and the like. There are also some portions with different dimensional relations and ratios among the drawings. Illustration of and assignment of reference signs to some constituent elements are omitted. The direction toward an object is referred to as "upward."

First Embodiment

Figure 1:
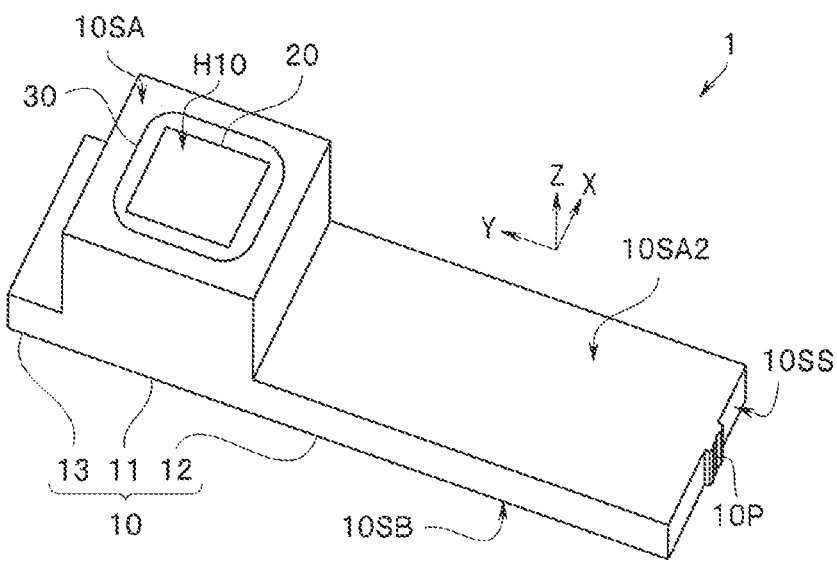
FIG. 1 is a perspective view of an image pickup unit of a first embodiment.
Figure 2:
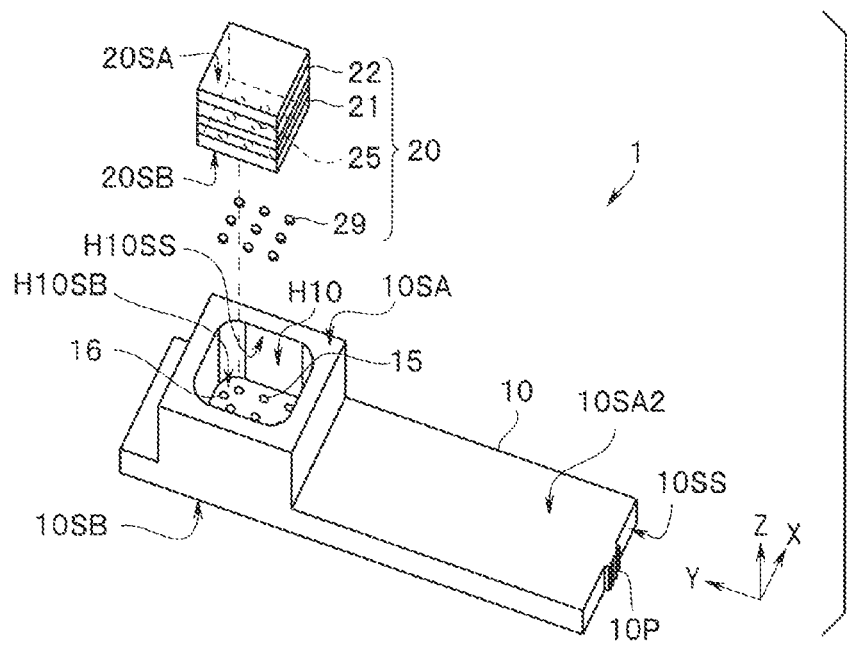
FIG. 2 is an exploded perspective view of the image pickup unit of the first embodiment.

An image pickup unit 1 of the present embodiment shown in FIG. 1 and FIG. 2 includes a three-dimensional wiring board 10, a stacked device 20, and a resin 30. Note that in FIG. 2, the resin 30 is not shown.

The stacked device 20 includes a light receiving surface 20SA and a back surface 20SB on a side opposite to the light receiving surface 20SA, and includes, on the back surface 20SB, external electrodes 25 that output an image pickup signal. The stacked device 20 in a substantially rectangular parallelepiped shape includes an optical system 22 in which a plurality of optical devices are stacked and an image pickup device (image sensor) 21. The optical device is, for example, a hybrid lens device (composite device) including a glass plate and a resin lens or an IR cut filter device.

The configuration of the optical system 22, that is, the configuration (thickness, shape), the type, the number, and the stacking order of the optical devices may be modified in various ways in accordance with the specification. A patterned light-shielding film may be disposed, as an aperture, on a principal surface of any one of the optical devices.

The stacked device 20 is produced using the wafer-level packaging method that dices a bonded wafer in which a stacked wafer composed of a plurality of optical device wafers each including a plurality of optical devices and a plurality of image pickup device wafers including a plurality of image pickup devices are bonded. Therefore, the stacked device 20 is in a rectangular parallelepiped shape. The stacked device 20 may be produced using the wafer-level packaging method that dices a bonded wafer in which a plurality of image pickup devices are adhesively bonded to a stacked wafer.

The image pickup device 21 with a silicon base material includes a light receiving portion composed of a CCD or the like. The stacked device 20 (image pickup device 21) includes solder bumps 29 on the external electrodes 25 on the back surface 20SB. At least one semiconductor device that processes an image pickup signal may be stacked on a lower surface of the image pickup device 21. In the stacked device with the semiconductor device stacked, the electrodes on a lower surface of the semiconductor device are the external electrodes 25. A cover glass may be disposed on an upper surface of the image pickup device 21.

The three-dimensional wiring board 10 (hereinafter, referred to as a "wiring board 10") includes a first principal surface 10SA, a side surface 10SS orthogonal to the first principal surface 10SA, and a second principal surface 10SB on a side opposite to the first principal surface 10SA. The first principal surface 10SA includes a recess H10. The recess H10 includes four wall surfaces H10SS and a bottom surface H10SB. Of the four wall surfaces H10SS, two side surfaces H10SS are parallel to the direction of the side surface 10SS relative to the recess H10 (first direction: Y-direction in the drawing). An opening of the recess H10 is in a substantially rectangular shape with curved corners, but may be in a rectangular shape.

The wiring board 10 includes a main portion 11 including the recess H10, and an extending portion 12 including a third principal surface 10SA2 that is parallel to the first principal surface 10SA and that has a distance from the second principal surface 10SB that is shorter as compared to the first principal surface 10SA. A side surface of the extending portion 12 is the side surface 10SS. The wiring board 10 also includes an extending portion 13 on a side opposite to the extending portion 12 across the main portion 11. As long as the extending portion 12 includes the side surface 10SS having a gate cut (projection) 10P described later, the third principal surface 10SA2 may not be parallel to the first principal surface 10SA, for example. The extending portion 12 may include a through hole or an electronic component may be mounted on the extending portion 12.

The wiring board 10 may not include the extending portions 12, 13. In the wiring board with no extending portions 12, 13, a side surface of the main portion 11 is the side surface 10SS.

Figure 3:
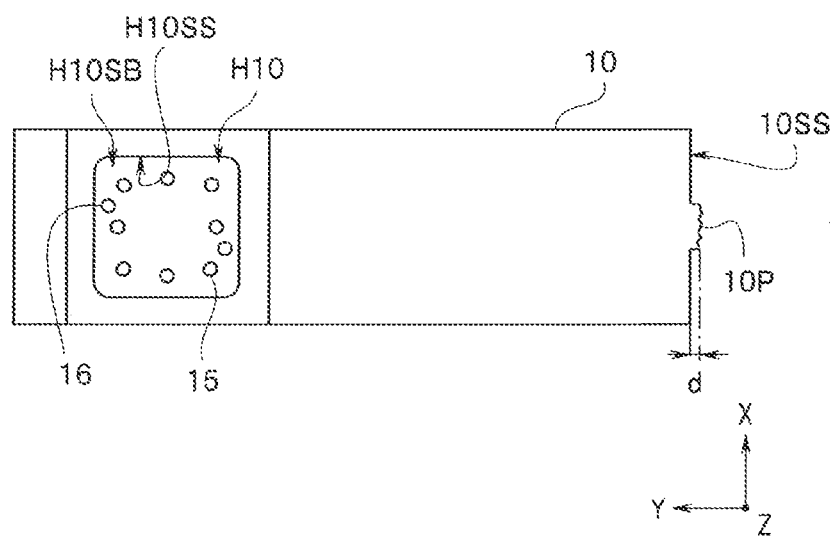
FIG. 3 is a top view of a MID of the image pickup unit of the first embodiment.
Figure 4:
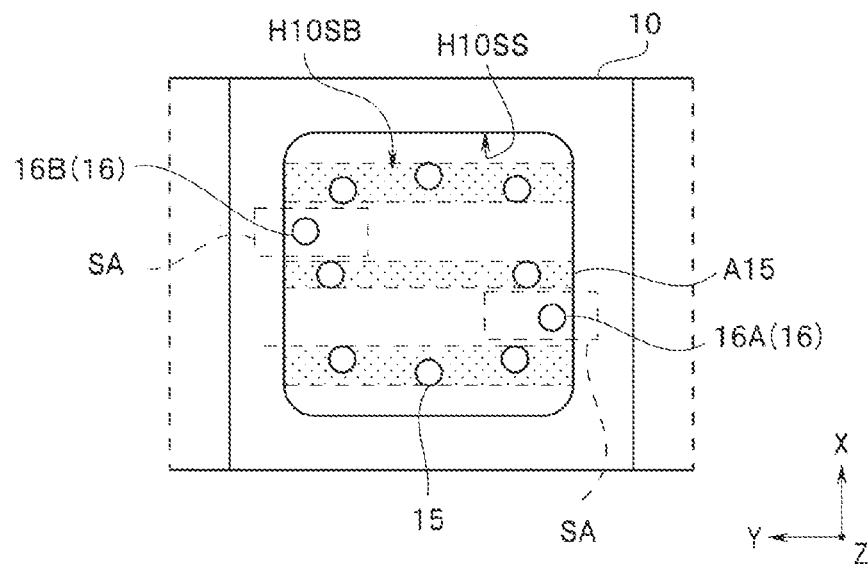
FIG. 4 is a top view of a part of the MID of the image pickup unit of the first embodiment.

As shown in FIG. 3 and FIG. 4, a plurality of bonding electrodes 15 and a plurality of alignment marks 16 (16A, 16B) are disposed on the bottom surface H10SB of the recess H10. Though not shown, the bonding electrodes 15 are electrically connected to electrodes on the second principal surface 10SB via surface wiring and through wiring. The bonding electrodes 15 may be connected to the electrodes on the second principal surface 10SB via wiring on the wall surface of the recess H10, wiring on the first principal surface 10SA, and wiring on the side surface of the main portion 11.

The stacked device 20 is disposed in the recess H10 of the wiring board 10. The external electrodes 25 of the stacked device 20 are bonded to the bonding electrodes 15 on the bottom surface H10SB of the recess H10 by means of the solder bumps 29. In other words, the light receiving portion of the image pickup device 21 is electrically connected to the electrodes on the second principal surface 10SB via the external electrodes 25, the solder bumps 29, the bonding electrodes 15, and the through wiring.

For example, the resin 30, which is, a thermosetting epoxy resin, seals a gap between the recess H10 and the stacked device 20. The resin 30 seals the stacked device 20 and simultaneously mitigates the stress applied to the stacked device 20. To prevent external light from entering through a side surface of the stacked device 20, it is preferable that the resin 30 should have a light shielding property by, for example, including light shielding particles.

The external electrodes 25 of the stacked device 20 and the bonding electrodes 15 on the bottom surface H10SB of the recess H10 of the wiring board 10 are aligned using an alignment apparatus such that first, at least two alignment marks 16 of the wiring board 10 fixed to a jig 50 (see FIG. 8) are detected, and then, the stacked device 20 or the wiring board 10 is moved so that the stacked device 20 and the wiring board 10 are in a predetermined relative position based on the positions of the alignment marks 16.

For example, the alignment apparatus calculates a correlation coefficient (similarity) with a template (size/shape of the alignment mark 16) based on an image of a search region SA (FIG. 4) of the bottom surface H10SB of the recess H10 that is photographed, and performs geometric pattern matching using the similarity as a scale to detect the alignment mark 16.

The wiring board 10 includes, on the side surface 10SS, the projection 10P projecting in the first direction (Y-direction in the drawing) parallel to the two side surfaces H10SS of the four wall surfaces H10SS of the recess H10. As will be described later, since the projection 10P shown in FIG. 3 is a gate cut, a projecting length (d) of the projection 10P differs among a plurality of wiring boards 10. Therefore, the initial positions of the plurality of wiring boards 10 fixed to the jig 50 vary.

The bonding electrode 15 and the alignment mark 16 are identical in shape and size due to restrictions on the specification of the stacked device 20 and the detecting capacity of the alignment apparatus. For example, the bonding electrode 15 is in a round shape with a diameter of 100 μm and the alignment mark 16 is also in a round shape with a diameter of 100 μm. Therefore, when the alignment mark 16 is detected, the bonding electrode 15 could be misrecognized as the alignment mark 16. Even when the bonding electrode 15 and the alignment mark 16 are substantially identical in shape and size, the bonding electrode 15 could be misrecognized as the alignment mark 16.

Note that substantially identical in shape and size means that the area of a superposed region where the bonding electrode 15 and the alignment mark 16 smaller than the bonding electrode 15 are virtually superposed on each other is, for example, 60% or greater of the area of the alignment mark 16. The bonding electrode 15 and the alignment mark 16 are in a substantially round shape including a circle or in a substantially rectangular shape including a rectangle.

As shown in FIG. 4, in the wiring board 10 of the image pickup unit 1, a first region A15 where the bonding electrode 15 is virtually moved in the first direction (Y-direction) and the alignment mark 16 are not superposed on each other on the bottom surface H10SB of the recess H10.

In a micro-image pickup unit, it is not easy to accurately perform positioning between the bonding electrodes on the bottom surface of the recess and the external electrodes on the back surface of the stacked device. Particularly in the MID, variations in the outer dimension inevitably occur. Therefore, the bonding electrode was occasionally misrecognized as the alignment mark for positioning.

However, in the image pickup unit 1, the search region SA of the alignment apparatus is set larger in the Y-direction considering the variations in the projecting amount of the projection 10P. Meanwhile, by setting the search region SA so as not to include the first region A15, the bonding electrode 15 is not misrecognized as the alignment mark 16. Since the stacked device 20 and the wiring board 10 can be easily aligned, the image pickup unit 1 can be easily manufactured.

<Method of Manufacturing Image Pickup Unit>

Figure 5:
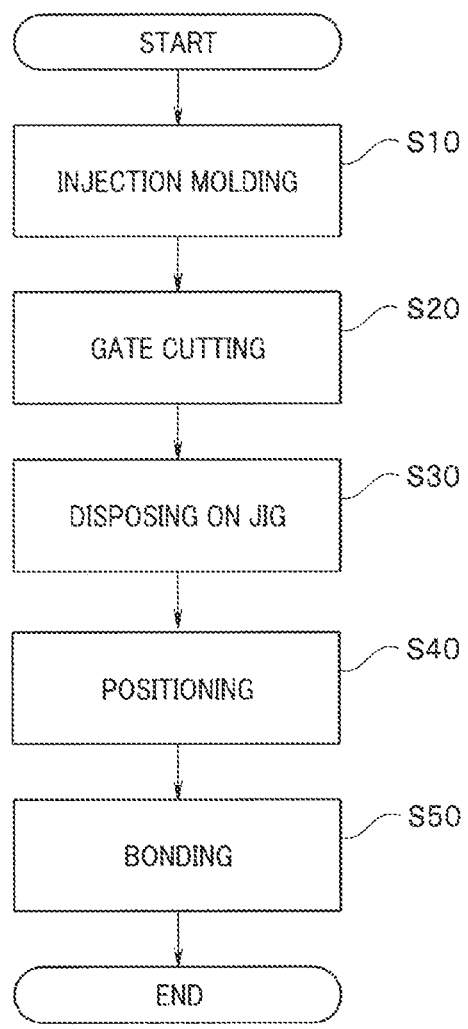
FIG. 5 is a flowchart of a method of manufacturing the image pickup unit of the first embodiment.

Following a flowchart of FIG. 5, a method of manufacturing the image pickup unit 1 will be described.

<Step S10> Injection Molding

Figure 6:
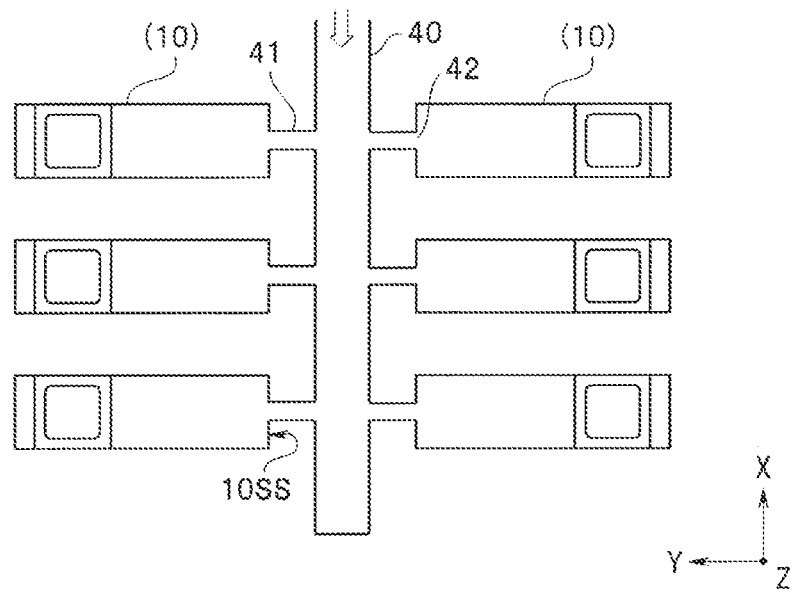
FIG. 6 is a plan view for explaining a method of manufacturing the MID of the image pickup unit of the first embodiment.

As shown in FIG. 6, the plurality of wiring boards 10 are produced using the injection molding method. A MID resin is injected from gates 42 into a mold (not shown) including the shape of a plurality of three-dimensional wiring boards, via a sprue 40 through runners 41. A plurality of molded bodies removed from the mold, which become the plurality of wiring boards 10, are connected by means of the sprue 40 and the runners 41.

The surface of the molded bodies formed of the MID resin is irradiated with a laser so that a region having a catalytic activity for electroless plating is formed. Further, a through hole is formed on the bottom surface of the recess H10. Thereafter, the molded bodies are subjected to an electroless plating treatment, so as to become the wiring boards 10 on which the bonding electrodes 15, the alignment marks 16, and the like are disposed.

As already described, the wiring board 10 includes the first principal surface 10SA and the side surface 10SS orthogonal to the first principal surface 10SA, and includes the bonding electrodes 15 and the alignment marks 16 on the bottom surface H10SB of the recess H10 on the first principal surface 10SA.

<Step S20> Gate Cutting

Figure 7:
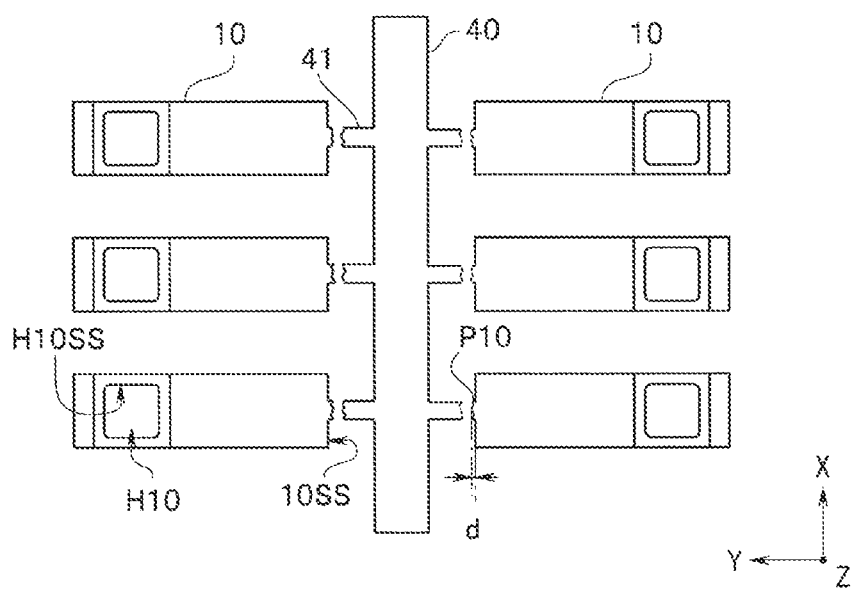
FIG. 7 is a plan view for explaining the method of manufacturing the MID of the image pickup unit of the first embodiment.

As shown in FIG. 7, the plurality of wiring boards 10 that are connected by means of the runners 41 are cut at the respective gates 42 to be made into individual pieces of the wiring boards 10. Therefore, the wiring board 10 includes, on the side surface 10SS, the gate cut 10P that is a projection projecting in the first direction parallel to the wall surface H10SS of the recess H10.

<Step S30> Disposing on Jig

Though not shown, the stacked device 20 in a rectangular parallelepiped shape is produced using the wafer-level packaging method that dices the bonded wafer in which the plurality of image pickup devices are bonded to the stacked wafer composed of the plurality of optical device wafers each including the plurality of optical devices. The stacked device 20 includes the solder bumps 29 on the external electrodes 25 on the back surface 20SB.

Figure 8:
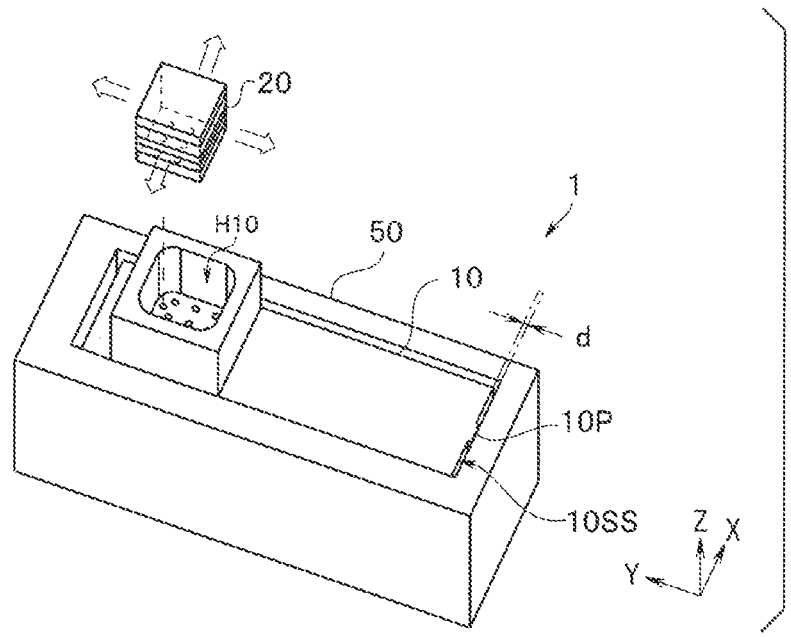
FIG. 8 is a perspective view for explaining the method of manufacturing the image pickup unit of the first embodiment.

As shown in FIG. 8, the wiring board 10 is fixed to the jig 50. The jig 50 may be a part of the alignment apparatus. At this time, the gate cut 10P of the wiring board 10 abuts on one surface of the jig 50.

As already described, the projecting amount d of the gate cut 10P from the side surface 10SS is not constant among the plurality of wiring boards 10.

<Step S40> Positioning

While moving at least one of the wiring board 10 or the stacked device 20, the positioning between the bonding electrodes 15 of the wiring board 10 and the external electrodes 25 of the stacked device 20 is performed.

First, the alignment mark 16 is detected. Depending on the shape of the alignment mark 16, only one alignment mark 16 may be detected, but to improve the accuracy, it is preferable that at least two alignment marks 16 should be detected.

When the alignment mark 16 is detected, the positions of the bonding electrodes 15 in predetermined relative positions with respect to the position of the alignment mark 16 are presumed. With a state in which the positions of the external electrodes 25 of the stacked device 20 are aligned so as to be superposed on the presumed positions of the bonding electrodes 15 of the wiring board 10, the stacked device 20 is inserted into the recess H10 of the wiring board 10.

For example, from the positions of the two alignment marks 16 (X-coordinate value, Y-coordinate value) of the wiring board 10 fixed to the jig on a stage of the alignment apparatus, XY coordinates 15P of two of the plurality of bonding electrodes 15 are presumed. A retaining member retaining the stacked device 20 moves the positions of the external electrodes 25 to the XY coordinates 15P and then moves the stacked device 20 in a Z-direction, so that with the aligned state, the stacked device 20 is inserted into the recess H10 of the wiring board 10. Note that for temporarily fixing the stacked device 20 to the recess H10, an adhesive may be used.

The search region SA of the alignment apparatus is set so as not to include the first region A15. Therefore, the bonding electrode 15 is not misrecognized as the alignment mark 16.

<Step S50> Bonding

With the state in which the wiring board 10 and the stacked device 20 are positioned, e.g., the state of temporary fixing, a reflow heating treatment is performed and the external electrodes 25 and the bonding electrodes 15 are bonded by means of the solder bumps 29. Thereafter, the resin 30 is injected into a gap between the recess H10 and the stacked device 20 and then, curing treatment is performed. In bonding by means of the solder bumps 29, a solder paste may be applied to the external electrodes 25 in advance.

In the method of manufacturing the image pickup unit 1 of the present embodiment, positioning between the wiring board 10 and the stacked device 20 is easy.

<Modifications of First Embodiment>

Since image pickup units 1A, 1B of modifications 1, 2 are similar to and have the same effects as the effects of the image pickup unit 1, the components having the same functions are assigned the same reference signs and the description will be omitted.

<Modification 1>

Figure 9:
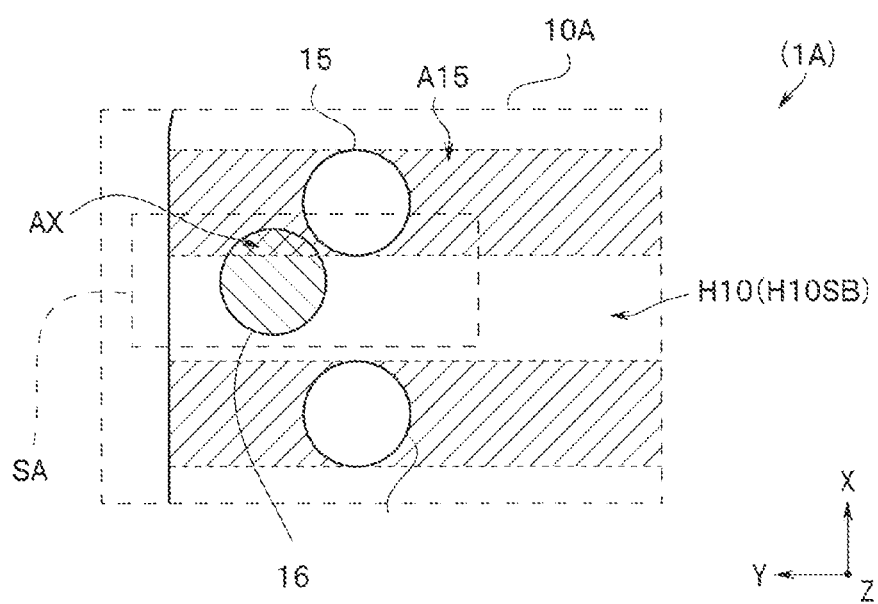
FIG. 9 is a top view of a part of a MID of an image pickup unit of a modification 1 of the first embodiment.

As shown in FIG. 9, in a wiring board 10A of the image pickup unit 1A of the present modification, a superposed region AX in which the first region A15 where the bonding electrode 15 is virtually moved in the first direction (Y-direction) and the alignment mark 16 are superposed on each other is on the bottom surface H10SB of the recess H10.

However, the area of the superposed region AX is 20% of the area of the alignment mark 16.

Since the search region SA of the alignment apparatus includes the first region A15, but does not entirely include the bonding electrode 15, the bonding electrode 15 is not misrecognized as the alignment mark 16.

Note that to prevent the misrecognition, the area of the superposed region AX is preferably less than 50%, particularly less than 30%, of the area of the alignment mark 16.

<Modification 2>

Figure 10:
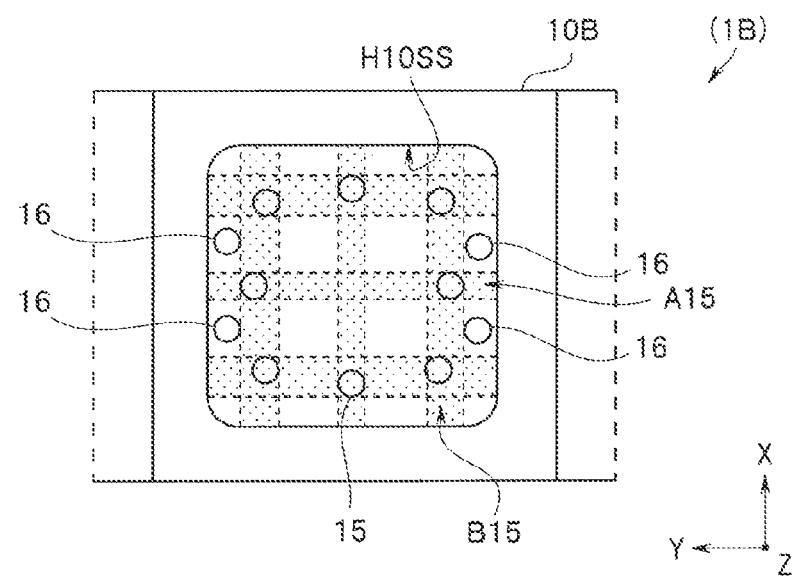
FIG. 10 is a top view of a part of a MID of an image pickup unit of a modification 2 of the first embodiment.

As shown in FIG. 10, in a wiring board 10B of the image pickup unit 1B of the present modification, the first region A15 where the bonding electrode 15 is virtually moved in the first direction (Y-direction) and a second region B15 where the bonding electrode 15 is virtually moved in a second direction (X-direction) orthogonal to the first direction (Y-direction), and the alignment mark 16 are not superposed on each other.

The search region (not shown) of the alignment apparatus does not include the first region A15 or the second region B15. Therefore, in the image pickup unit 1B, the bonding electrode 15 is far less likely to be misrecognized as the alignment mark 16 than in the image pickup unit 1.

Note that even when a part of the alignment mark 16 is superposed on the first region A15 and the second region B15, as long as the total of the area of the first region A15 and the alignment mark 16 superposed on each other and the area of the second region B15 and the alignment mark 16 superposed on each other is less than 50% of the area of the alignment mark 16, the bonding electrode 15 is not misrecognized as the alignment mark 16.

Second Embodiment

Figure 11:
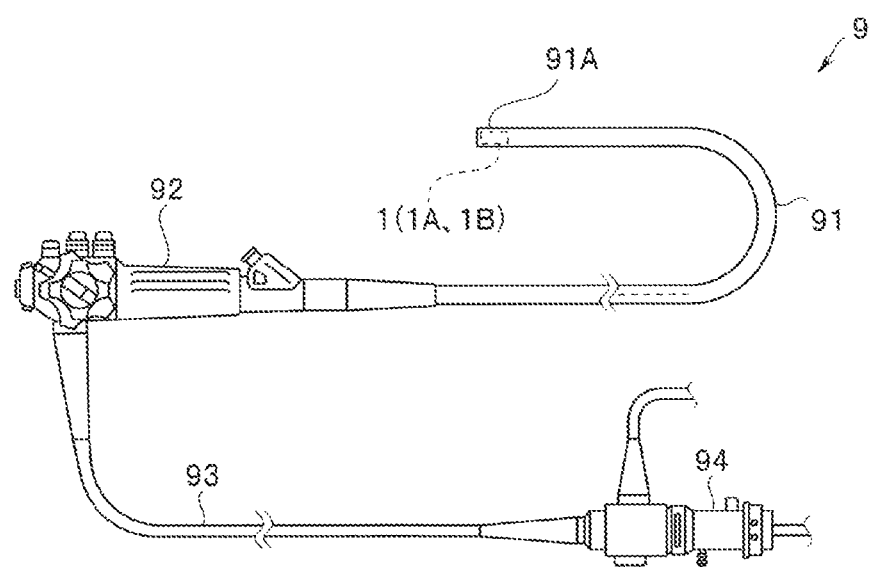
FIG. 11 is a perspective view of an endoscope of a second embodiment.

An endoscope 9 of the present embodiment shown in FIG. 11 includes an insertion portion 91, an operation portion 92, a universal cord 93, and an endoscope connector 94. The insertion portion 91 in an elongated tubular shape is inserted into a body cavity of a living body.

The endoscope 9 includes the image pickup unit 1, 1A, or 1B that is disposed in a distal end portion 91A of the insertion portion 91. As already described, since the image pickup units 1, 1A, and 1B are easily manufactured, the endoscope 9 is easily manufactured.

Note that the three-dimensional wiring board including the recess H10 where the stacked device 20 is disposed may be formed by, for example, processing using a 3D printer or cutting processing, without being limited to the MID. The material of the three-dimensional wiring board is not limited to resin, but may be ceramics or glass epoxy.

The endoscope 9 is a flexible endoscope for medical use, but the endoscope of another embodiment may be an endoscope for industrial use, or a rigid endoscope including a rigid straight tube as the insertion portion.

The present invention is not limited to the aforementioned embodiments and the like, and various changes, modifications, and the like can be made within the scope without changing the gist of the present invention.

What is claimed is:

1. An image pickup unit comprising:
   a stacked device in a substantially rectangular parallelepiped shape including:
      a light receiving surface and a back surface on a side opposite to the light receiving surface; and
      an external electrode, on the back surface, that outputs an image pickup signal; and
   a three-dimensional wiring board including:
      a first principal surface and a side surface orthogonal to the first principal surface;
      a bonding electrode and an alignment mark on a bottom surface of a recess on the first principal surface; and
      a projection, on the side surface, projecting in a first direction parallel to a wall surface of the recess,
   wherein
      the external electrode of the stacked device that is disposed in the recess is bonded to the bonding electrode, and
      on the bottom surface, an area of a region in which a first region where the bonding electrode is virtually moved in the first direction and the alignment mark are superposed on each other is less than 50% of an area of the alignment mark.

2. The image pickup unit according to claim 1, wherein the alignment mark is not superposed on the first region.

3. The image pickup unit according to claim 1, wherein the projection is a gate cut.

4. The image pickup unit according to claim 1, wherein the alignment mark is substantially identical in shape and size to the bonding electrode.

5. The image pickup unit according to claim 1, wherein the alignment mark and the bonding electrode are in a substantially rectangular shape or a substantially round shape.

6. The image pickup unit according to claim 1, wherein a total of the area of the region in which the first region and the alignment mark are superposed on each other, and an area of a region in which a second region where the bonding electrode is virtually moved in a second direction orthogonal to the first direction and the alignment mark are superposed on each other is less than 50% of the area of the alignment mark.

7. An endoscope comprising an image pickup unit, the image pickup unit comprising:

a stacked device in a substantially rectangular parallelepiped shape including:
  a light receiving surface and a back surface on a side opposite to the light receiving surface; and
  an external electrode, on the back surface, that outputs an image pickup signal; and
a three-dimensional wiring board including:
  a first principal surface and a side surface orthogonal to the first principal surface;
  a bonding electrode and an alignment mark on a bottom surface of a recess on the first principal surface; and
  a projection, on the side surface, projecting in a first direction parallel to a wall surface of the recess,
  wherein
  the external electrode of the stacked device that is disposed in the recess is bonded to the bonding electrode, and
  on the bottom surface, an area of a region in which a first region where the bonding electrode is virtually moved in the first direction and the alignment mark are superposed on each other is less than 50% of an area of the alignment mark.

8. A method of manufacturing an image pickup unit, comprising:
  producing a plurality of three-dimensional wiring boards each including a first principal surface and a side surface orthogonal to the first principal surface, and a plurality of bonding electrodes and an alignment mark on a bottom surface of a recess on the first principal surface, using an injection molding method in which resin is injected into a mold via runners respectively extending from the side surfaces and then through irradiation with a laser and film-forming by plating;
  cutting the plurality of three-dimensional wiring boards at each of the runners into individual pieces of the three-dimensional wiring boards each including, on the side surface, a gate cut projecting in a first direction parallel to a wall surface of the recess;
  causing the gate cut of each of the three-dimensional wiring boards to abut on one surface of a jig;
  on the bottom surface, using the alignment mark with an area of a region superposed on a first region where the bonding electrode is virtually moved in the first direction is less than 50% of an area of the alignment mark, performing positioning between the bonding electrode and an external electrode of a stacked device in a substantially rectangular parallelepiped shape that includes a light receiving surface and a back surface, and on the back surface, the external electrode that outputs an image pickup signal, and
  bonding the external electrode and the bonding electrode.

* * * * *